United States Patent
DeBusk

Patent Number: 5,725,517
Date of Patent: Mar. 10, 1998

[54] ABSORBENT WOVEN ARTICLE INCLUDING RADIOPAQUE ELEMENT WOVEN THEREIN AND ANCHORED AT THE ENDS THEREOF

[75] Inventor: Autry O. V. DeBusk, Knoxville, Tenn.

[73] Assignee: DeRoyal Industries, Inc., Powell, Tenn.

[21] Appl. No.: 711,543

[22] Filed: Sep. 10, 1996

Related U.S. Application Data

[63] Continuation-in-part of Ser. No. 640,486, May 1, 1996, which is a continuation-in-part of Ser. No. 539,677, Oct. 5, 1995, Pat. No. 5,575,781.

[51] Int. Cl.⁶ .............................. A61F 13/15; A61F 13/20
[52] U.S. Cl. ................................................ 604/362
[58] Field of Search ........................ 604/358, 362, 604/385.1

[56] References Cited

U.S. PATENT DOCUMENTS

| | | | |
|---|---|---|---|
| 2,698,270 | 12/1954 | Mesek | 154/93 |
| 3,097,649 | 7/1963 | Gray | 128/296 |
| 3,301,257 | 1/1967 | Crowe, Jr. et al. | 128/296 |
| 3,422,816 | 1/1969 | Robinson et al. | 128/296 |
| 3,464,415 | 9/1969 | Brownlee | 128/296 |
| 3,698,393 | 10/1972 | Stone | 128/296 |
| 3,756,241 | 9/1973 | Patience | 128/296 |
| 3,867,935 | 2/1975 | Eisdorfer et al. | 128/156 |
| 3,911,922 | 10/1975 | Kliger | 128/296 |
| 3,965,907 | 6/1976 | Hardy et al. | 128/296 |
| 4,068,666 | 1/1978 | Shiff | 128/290 |
| 4,205,680 | 6/1980 | Marshall | 128/296 |
| 4,262,251 | 4/1981 | Shen | 604/362 |
| 4,639,253 | 1/1987 | Dyer et al. | 604/362 |
| 4,917,694 | 4/1990 | Jessup | 604/362 |
| 4,935,019 | 6/1990 | Papp, Jr. | 604/362 |
| 5,041,103 | 8/1991 | Rupinskas | 604/362 |
| 5,045,080 | 9/1991 | Dyer et al. | 604/362 |

FOREIGN PATENT DOCUMENTS 1171260  7/1984  Canada.

Primary Examiner—John G. Weiss
Assistant Examiner—Ki Yong O
Attorney, Agent, or Firm—Paul E. Hodges, P.C.

[57] ABSTRACT

A woven absorbent article, useful in medical application, including at least one yarn-like radiopaque element extending along the length dimension and fully from one end to the opposite end of the absorbent article and having its opposite ends anchored to the absorbent article by means of multiple folds at each of the ends of the absorbent article. Preferably, the radiopaque element is incorporated into the woven article in the form of a warp yarn of the weave thereof. A method for the manufacture of the article is disclosed.

5 Claims, 2 Drawing Sheets

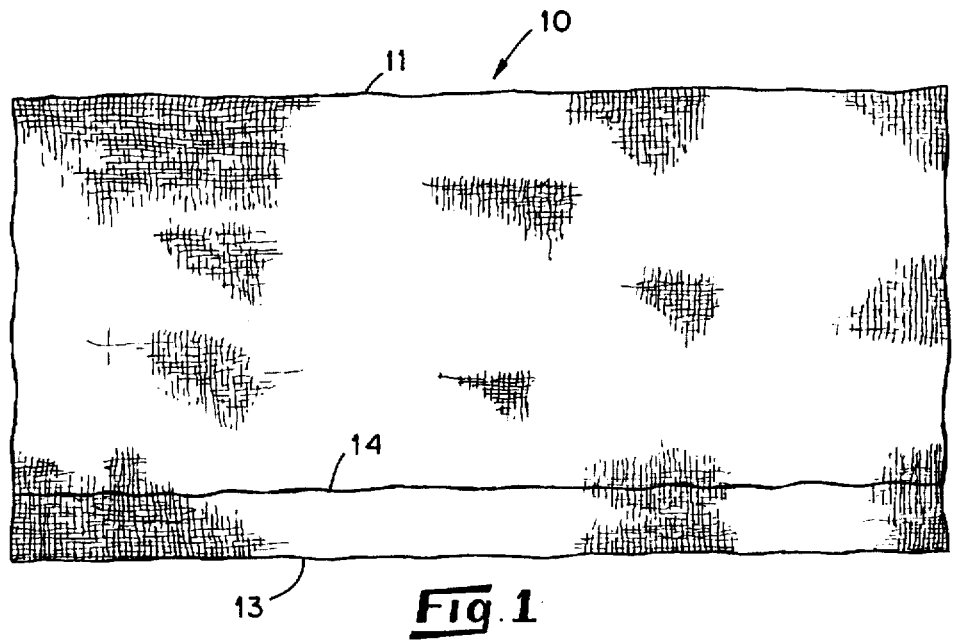
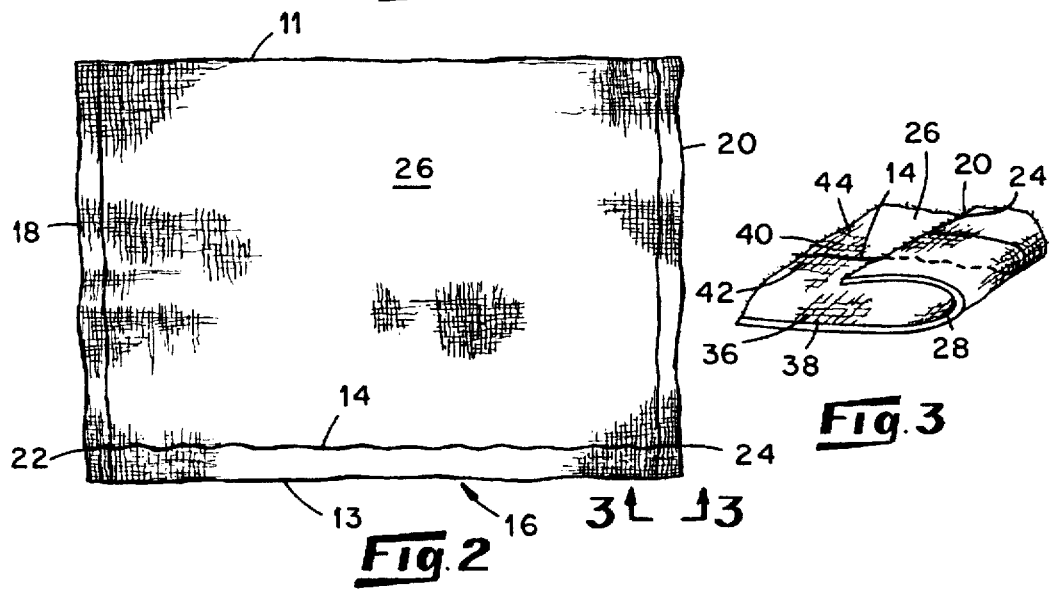
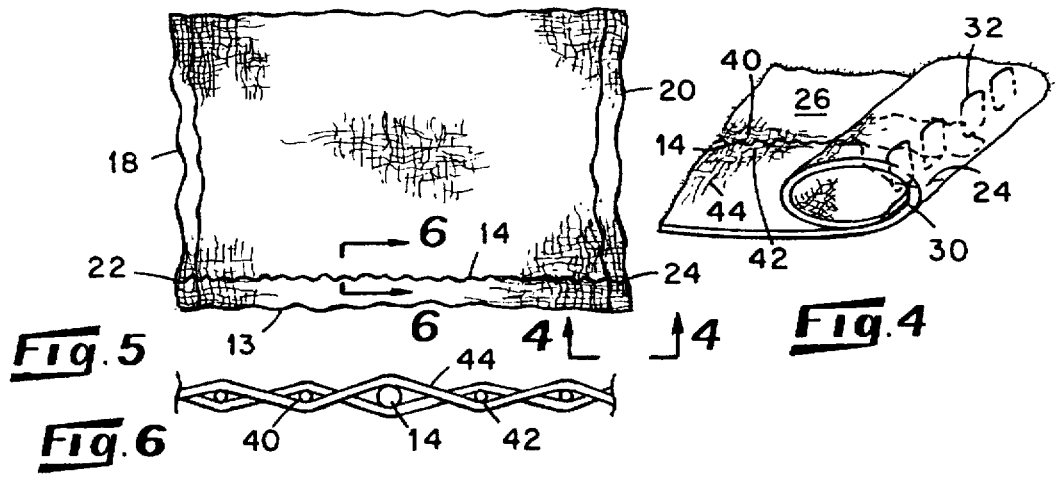

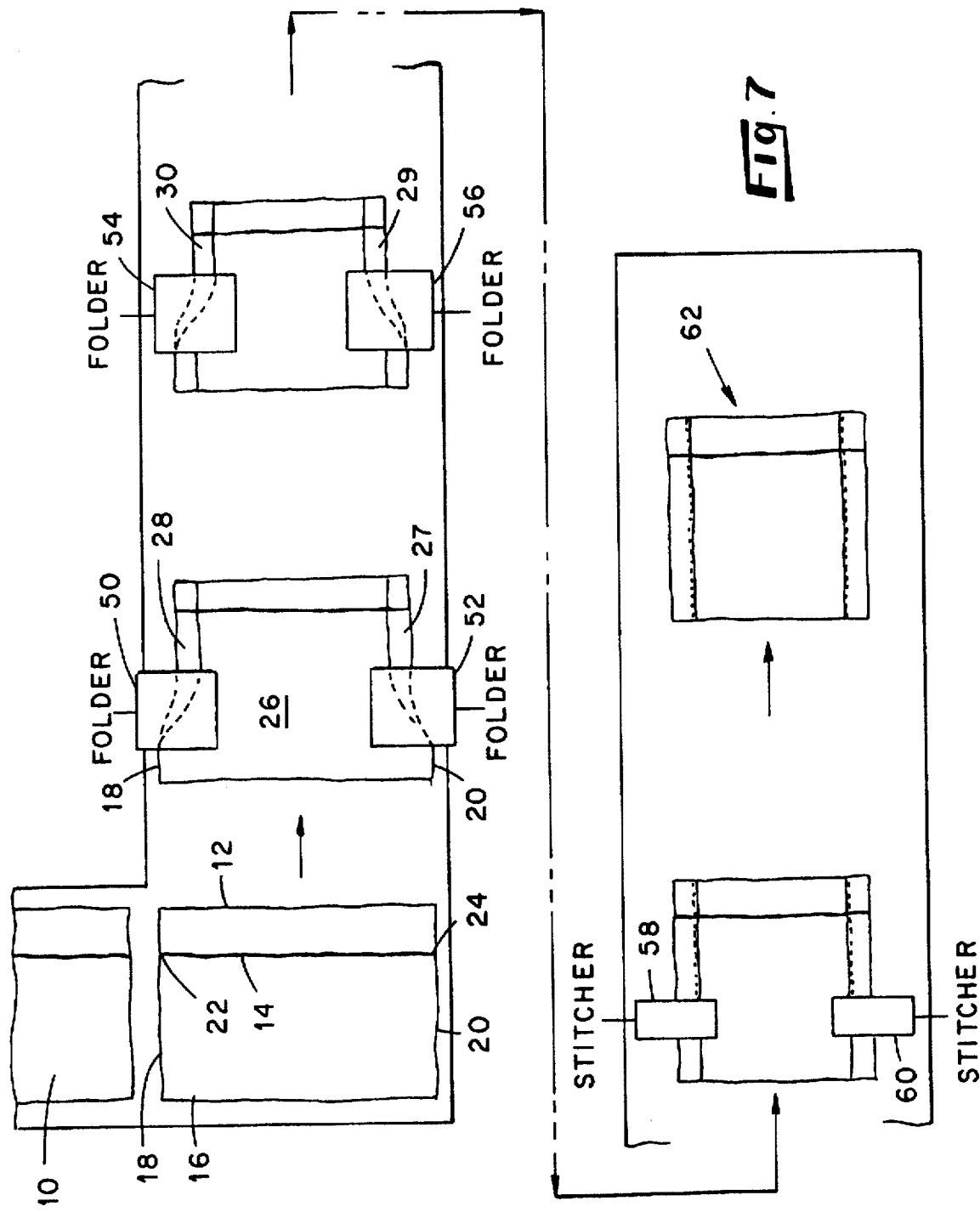

ABSORBENT WOVEN ARTICLE INCLUDING RADIOPAQUE ELEMENT WOVEN THEREIN AND ANCHORED AT THE ENDS THEREOF

CROSS-REFERENCE TO RELATED APPLICATIONS

This invention is a continuation-in-part of application Ser. No. 08/640,486 still pending which is a continuation-in-part of application Ser. No. 08/539,677, now U.S. Pat. No. 5,575,781 filed Oct. 5, 1995; each of the aforesaid applications being incorporated herein in their respective entireties.

STATEMENT REGARDING FEDERALLY SPONSORED RESEARCH OR DEVELOPMENT

"Not Applicable"

FIELD OF INVENTION

This invention relates to absorbent articles which are useful in medical applications, and particularly to a woven absorbent article including at least one radiopaque element incorporated therein.

BACKGROUND OF INVENTION

Absorbent articles, such as laparotomy sponges and huck towels are commonly known articles in medical care facilities. These articles are used variously to absorb body fluids, as wipes for cleaning wounds, as drapes for shielding off a body area during the course of performing a medical procedure within the body area, and many other uses. In certain of these applications, it is required that the absorbent article include an element which is detectable by X-ray examination.

Radiopaque elements commonly comprise flat strips or lengths of an elastomeric material that is impregnated with a material, such as barium sulfate, which is opaque to X-rays, such as barium sulfate. These radiopaque elements exhibit a relatively low coefficient of friction hence are difficult to contain or maintain in a desired position on or in a woven absorbent article.

It is therefore an object of the present invention to provide a woven absorbent article including a yarn-like radiopaque element incorporated therein and wherein the opposite ends of the radiopaque element are anchored within respective opposite edges of the absorbent product.

It is another object of the present invention to provide a method for the incorporation of a yarn-like radiopaque element within a woven absorbent article.

BRIEF SUMMARY OF INVENTION

In accordance with the present invention there is provided a woven absorbent article, useful in medical applications, including at least one yarn-like radiopaque element incorporated therein. In accordance with one aspect of the present invention, the yarn-like element extends along the length dimension and substantially fully from one end to the opposite end of the absorbent article and preferably is incorporated within the body of the absorbent article in the form of a warp yarn of the weave of the absorbent article. The opposite ends of the radiopaque element are anchored to the absorbent article by means of multiple folds at each of the ends of the absorbent article, these folds mechanically capturing therein the ends of the radiopaque element to anchor these element ends within the absorbent article. Further, the folds at each end of the absorbent article function to encapsulate the raw ends of the radiopaque element and protect against the possibility that an exposed raw end of the element might become a source of body tissue agitation or damage to a patient, or possibly break away from the woven article and become a source of possible granuloma development within a patient.

The absorbent article of the present invention may take the form of a medical sponge, e.g. a laparotomy sponge, or a surgical towel (huck towel), the body of which is formed by a weaving process.

BRIEF DESCRIPTION OF DRAWINGS

FIG. 1 is a schematic representation of one embodiment of a portion of an absorbent woven web including a yarn-like radiopaque element incorporated therein in accordance with the present invention;

FIG. 2 is a schematic representation of a woven absorbent article formed from a cut length of the web of FIG. 1 and including inwardly folded opposite ends of the article;

FIG. 3 is a schematic representation of a portion of one end of a cut length of the web of FIG. 1 and depicting a first inward fold of the end of a woven article as depicted in FIG. 2, and including one end of a yarn-like radiopaque element disposed within the first fold;

FIG. 4 is a schematic representation of the first fold depicted in FIG. 3 as further folded inwardly of the woven article to define a second fold that includes the first fold and the end of the radiopaque element therein;

FIG. 5 is a schematic representation of the woven absorbent article of FIG. 2 after the article has been subjected to a washing;

FIG. 6 is a schematic representation, in section, taken generally along the line 6—6 of FIG. 5 and depicting the incorporation of a yarn-like radiopaque element in the weave pattern of the woven web of the present invention; and FIG. 7 is a diagrammatic representation of one embodiment of an apparatus for carrying out the method of the present invention.

DETAILED DESCRIPTION OF INVENTION

In FIG. 1 there is depicted one embodiment of a woven web 10 from which there are cut individual lengths 16 (FIG. 2), each of which constitutes the body 12 of the absorbent article of the present invention. The weave pattern of the web may vary from a very open weave such as is employed in the manufacture of gauze, to a relatively tight weave such as is employed in the manufacture of huck towels (surgical towels). In like manner, the denier of the yarns may vary widely, depending upon the desired end product. As taken from a loom, the web 10 includes selvege side edges 11 and 13.

In accordance with the present invention, there is incorporated into the weave pattern of the absorbent article at least one yarn-like radiopaque element 14. In a preferred embodiment, this radiopaque element is incorporated as a warp yarn in the weave pattern so that in the weaving of a web, the radiopaque element extends substantially parallel to the length dimension of the web. As depicted in FIG. 2, when the web is cut into discrete lengths 16, each length includes a radiopaque element that extends fully between the cut ends 18 and 20 of each cut length of web. This results in two cut, i.e. raw, ends 22 and 24, of the radiopaque element.

In accordance with one aspect of the present invention, each of the ends 18 and 20 of the length of web 16 is folded inwardly of the body of the length of web and in overlying relationship to a top surface 26 of the length of web to define a first fold 28 (See FIGS. 3 and 7). This first fold includes therein a cut end 24 of the radiopaque element. This first fold is thereafter further folded inwardly of the body of the length of web and again in overlying relationship to the top surface 26 of the length of web to define a second fold 30 (See FIG. 4). This second fold encapsulates therein the first fold so that the cut ends of the warp yarns of the woven web and the cut end 24 of the radiopaque element are captured mechanically internally of the second fold. The first and second folds are secured in position relative to the top surface of the body of the length of web as by stitching 32, or other means such as gluing. Importantly, this twice inward folding of the end 24 of the radiopaque element 14 serves to anchor the end 24 of the element to the body of the length of web at the cut end 20 of the web length 16. In the present invention the opposite cut end 18 of the web length 16 is likewise folded inwardly of and onto the top surface 26 of the web length 16 employing further double folds 27 and 29 (see FIG. 7) which are essentially a mirror image of the folds 28 and 30. The latter inward folding of the cut end 18 of the web length serves to anchor the cut end 22 of the radiopaque element to the web length so that the element 14 is securely anchored at its opposite ends 22 and 24 to the web length 16. Thus, the element is anchored within the weave pattern of the web and can not work itself partly or wholly out of the weave pattern of the web even during use of the absorbent article. Further, the cut end of the radiopaque element is so captured within the folds as precludes a portion of the end of the element from breaking loose and becoming a potential hazard to the patient in the form of a source of a possible granuloma. Still further, the multiple inward folds position the cut ends of the absorbent warp yarns inside the folds, thereby preventing these cut ends from being exposed during use of the absorbent article where they could irritate or damage a patient's body tissue.

In a preferred embodiment of the present absorbent article, the weft and warp yarns 36 and 38, respectively, of the body of the woven web may be of any absorbent material which is suitable for medical applications. Cotton fiber yarns are preferred, but absorbent synthetic fiber yarns or combinations of cotton and absorbent synthetic fiber yarns may be used. Conventional weave patterns may be employed, depending upon the intended end use of the absorbent article. For example, the weave pattern described in copending application Ser. No. 08/539,677, may be employed when the absorbent article is intended to be used as a laparotomy sponge. If the absorbent article is intended to be used as a surgical towel or drape, the weave pattern disclosed in copending application Ser. No. 08/640,486 may be employed.

The yarn-like radiopaque element 14 of the present invention may comprise a monofilament of an elastomeric material which is impregnated with barium sulfate as is well known in the art. These elastomeric monofilaments exhibit a coefficient of friction which is materially less than the coefficient of friction of known absorbent yarns. Accordingly, as noted, these monofilaments have not heretofore known to have been successfully incorporated into a woven absorbent article other than by attaching the monofilament to a surface of the woven product. Prior attachment teaching us include the use of an adhesive or by thermobonding in which either a thermoplastic monofilament and/or thermoplastic yarns are heated to their melting joint and held under pressure until the thermoplastic resolidifies. Alternatively, the radiopaque element may comprise a bundle of radiopaque monofilaments which are helically wrapped by a substantially non-resilient yarn such as a cotton or polyester yarn as described in U.S. Pat. No. 5,112,325. In any event, the radiopaque element must have sufficient strength in its length direction as will permit it to be processed through a conventional loom. When employing a radiopaque element of the type disclosed in U.S. Pat. No. 5,112,325 it is of especial importance that the cut ends of the yarn-like element be captured and fully encapsulated within the folds of the ends of the woven web because of the multiplicity of ends of the many monofilaments which make up the wrapped radiopaque element.

Further, when the absorbent article is intended to be used as a sponge, the weave pattern of the web is very open to provide for enhanced rate of absorption and total absorptive capacity of the sponge. Because of the openness of this type weave pattern and the relatively low coefficient of friction of the elastomeric material of a radiopaque element, it is especially difficult to retain a yarn-like radiopaque element within the body of the woven web. This problem is compounded in that woven webs which are intended to be used as medical sponges must be washed to remove oils and/or other foreign materials from the web after it has been woven. This washing commonly includes a hot water wash which shrinks the absorptive yarns of the web, causing them to assume a crinkled appearance. This factor poses a difficult problem since the elastomeric radiopaque element does not shrink materially when washed, and therefore tends to retain its elongated straight length dimension. Heretofore it has not been possible to prevent the opposite ends of the nonshrinking radiopaque elements from projecting beyond the ends of the washed cut lengths of the woven web. The present inventor found, however, that this problem is obviated by capturing and anchoring the opposite ends of the radiopaque element within respective ones of the opposite ends of the cut length of woven web prior to washing of the web. When thus anchored, and by incorporating the radiopaque element as a yarn in the weave pattern of the woven web, the inventor further found that the length of the radiopaque element 14 between its opposite ends 22 and 24 is constrained by neighboring ones of the absorbent yarns, 40, 42 and 44, for example, and physically forced to assume much the same curved or crinkled shape as do the absorbent yarns of the web, thereby enhancing the degree of retention of the radiopaque element within the general plane of the absorbent article. By this means, the present invention further offers the advantage of more fully burying the radiopaque element within the individual yarns of the absorbent article where the radiopaque element is less likely to present an abrasive or otherwise undesirable surface to the body tissue of a patient when the absorbent article is in use. It has also been found that the assumption of a contorted profile by the radiopaque element enhances the recognition of the radiopaque element under X-ray examination.

With reference to FIG. 7, the method for the manufacture of the absorbent product of the present invention includes the steps of severing a length of woven web 10 into individual lengths 16, each length including a radiopaque element 14 extending from one end 18 to the opposite end 20 of the cut length of web. The cut length 16 is fed forwardly through a first and second folders 50 and 52 which turn the cut ends 18 and 20 inwardly of and onto the top surface 26 of the cut length 16 to define a first folds 28 and 27 along the opposite ends 18 and 20, respectively, of the cut length 16. The opposite cut ends 22 and 24 of the radiopaque element are captured in these first folds.

Thereupon, the cut length 16, with its first end folds is fed forwardly through second and third folders 54 and 56 which further turn the first folded ends 18 and 20 of the cut length 16 inwardly and onto the top surface 26 of the cut length 16 to define second folds 30 and 29. The opposite ends 22 and 24 of the radiopaque element, and the cut ends of the yarns of the ends 18 and 20 of the cut length 16, are thereby turned inwardly and mechanically captured within the second folds. This capture anchors the ends 22 and 24 of the radiopaque element within these second folds and prevents escape of the element ends from their position within the folds.

The cut length 16 with its twice folded opposite ends is thereupon fed forwardly through first and second stitchers 58 and 60 whereupon the folded ends of the cut length are secured in their folded positions along each of the ends of the cut length 16. The folded and stitched product 62 is passed to further operational stations as desired.

Whereas the present invention has been described in terms of the yarn-like radiopaque element comprising a warp yarn, it is to be recognized that the radiopaque element could be a weft yarn in the weave pattern. In any event, the radiopaque element extends substantially from one edge of the woven web to the opposite edge of the web, whether lengthwise of the web or transverse to the length of the web, and the ends of the radiopaque element are folded inwardly with their respective edges of the web as described hereinabove.

What is claimed:

1. An absorbent article useful in medical applications comprising a length of web having first and second ends and a top surface, said web being woven of absorbent yarns, at least one yarn-like radiopaque element having first and second opposite ends and being woven into said length of web and extending substantially fully between said first and second ends of said length of web, said radiopaque element including an elastomeric material impregnated with a material which is opaque to X-rays and having a coefficient of friction substantially less than the coefficient of friction of said absorbent yarns and being substantially more resistant to shrinkage in length than said absorbent yarns when said length of web is subjected to washing, at least said first end of said length of web being folded inwardly of said length of web and in overlying relationship to said top surface of said web to define a first fold, said first end of said radiopaque element being folded inwardly with said first fold, said at least first fold being further folded inwardly of said length of web and in overlying relationship to said top surface of said web to define a second fold that includes said first fold therein, said first end of said radiopaque element contained within said first fold being folded inwardly with said second fold, whereby said first and second ends of said radiopaque element are mechanically captured and anchored within first and second folds such that upon washing of said length of web said radiopaque element is caused to assume a nonstraight geometry while being constrained by neighboring ones of said absorbent yarns to the general plane of said web.

2. The woven absorbent article of claim 1 wherein said yarn-like radiopaque element is incorporated into the weave of the article as a warp yarn.

3. The woven absorbent article of claim 1 wherein said yarn-like radiopaque element is essentially fully resistant to shrinkage when washed in water.

4. The woven absorbent article of claim 3 wherein said absorbent yarns assume a non-straight attitude when washed in water.

5. The woven absorbent article of claim 1 wherein said yarn-like radiopaque element is physically constrained to a geometry similar to the geometry of the warp yarns of the weave.

* * * * *